United States Patent [19]

Dicker et al.

[11] Patent Number: 4,698,345

[45] Date of Patent: Oct. 6, 1987

[54] QUINOLINE DERIVATIVES AND THEIR USE AS ANTI-ASTHMATIC AGENTS

[75] Inventors: Ian D. Dicker; John L. Suschitzky, both of Loughborough, England

[73] Assignee: Fisons plc, Ipswich, England

[21] Appl. No.: 695,460

[22] Filed: Jan. 28, 1985

[30] Foreign Application Priority Data

Jan. 26, 1984 [GB] United Kingdom ............... 8402047

[51] Int. Cl.$^4$ ................ A61K 31/395; C07D 491/052
[52] U.S. Cl. .................................... 514/291; 514/411; 546/62; 546/89; 548/430; 548/431
[58] Field of Search .................... 546/62, 89; 514/291, 514/411; 548/430, 431

[56] References Cited

U.S. PATENT DOCUMENTS 4,419,352 12/1983 Cox et al. ............................ 514/291

FOREIGN PATENT DOCUMENTS 0037187 10/1981 European Pat. Off. ............. 546/89

OTHER PUBLICATIONS

Yale, Harry L., J. of Med. Chem., vol. 1, No. 2, (1959), pp. 121–131.
Goodman et al., The Pharmacological Basis of Therapeutics, 6 Ed., p. 28.

Primary Examiner—John M. Ford
Assistant Examiner—J. Richter
Attorney, Agent, or Firm—Marshall, O'Toole, Gerstein, Murray & Bicknell

[57] ABSTRACT

There are provided benzopyrans of formula I,

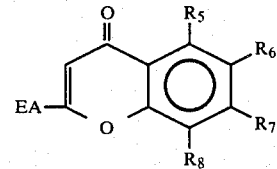

wherein the substituents, $R_5$–$R_8$ and EA are as defined in the specification. These compounds are useful as anti-asthmatic agents.

8 Claims, No Drawings

QUINOLINE DERIVATIVES AND THEIR USE AS ANTI-ASTHMATIC AGENTS

This invention relates to new benzopyrans, processes for their production and compositions containing them.

Benzodipyran dicarboxylic acid derivative having anti-allergic properties are disclosed in UK Patent No. 123007. Certain benzodipyran derivatives substituted by tetrazolyl groups and having anti-allergic properties are disclosed in UK Patent No. 1389827. Various pyranoquinoline dicarboxylic acids which also have anti-allergic activity are disclosed in UK Patent Nos. 2022078B and 2035312B. We have now found a new group of benzopyran derivatives which have advantageous properties over compounds specifically disclosed in the above patent specifications.

According to the invention there are provided benzopyrans of formula I,

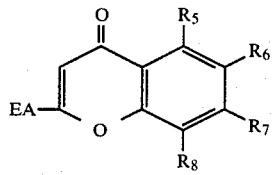

wherein an adjacent pair of $R_5$, $R_6$, $R_7$ and $R_8$ represent the chain $-X-CR_{12}R_{13}-CR_{14}R_{15}-NR_{20}-$ in which the chain is substituted by $-A_1E_1$, X represents $CR_{10}R_{11}$ or a single bond, and (a) $R_{14}$ and $R_{20}$ together form a single bond and optionally $R_{10}$ and $R_{12}$ together form a single bond, or (b) $R_{12}$ and $R_{14}$ together form a single bond, or (c) $R_{10}$, $R_{12}$ and $R_{14}$ each represent hydrogen; and the remainder of $R_{10}$, $R_{11}$, $R_{12}$, $R_{13}$, $R_{14}$, and $R_{15}$, which may be the same or different, independently represent hydrogen, alkyl, $NR_{21}COR_{22}$, CN or $C_nH_xF_{(2n+1-x)}$; in addition, a geminal pair of $R_{10}$, $R_{11}$, $R_{12}$, $R_{13}$, $R_{14}$, $R_{15}$, $R_{16}$, and $R_{17}$ together with the carbon atom to which they are attached, may represent $>C=O$ or $>C=N-OR_{23}$; also a vicinal pair of $R_{11}$, $R_{13}$ and $R_{15}$, may form the chain $-CH=CH-CH=CH-$ which is substituted by $A_1E_1$, A and $A_1$, which may be the same or different, represent a single bond, $(CH_2)_m$ or arylene, n represents an integer from 1 to 10 inclusive, x represents 0 or an integer from 1 to 2n inclusive, m represents an integer from 1 to 10 inclusive, when $R_{20}$ does not form a single bond with $R_{14}$, $R_{20}$ may represent hydrogen, alkyl, aryl or alkyl substituted by aryl, $R_{21}$, $R_{22}$, and $R_{23}$, which may be the same or different, independently represent hydrogen, alkyl or aryl;

the remainder of $R_5$, $R_6$, $R_7$ and $R_8$, which may be the same or different, each independently represent hydrogen, hydroxy, alkoxy, amino, halogen, nitro, cyano, alkyl, aryl or alkyl substituted by aryl, E and $E_1$, which may be the same or different, independently represent $-COOH$, or 5H-tetrazolyl, provided that when the chain $-X-CR_{12}R_{13}-CR_{14}R_{15}-NR_{20}-$ (i) represents a chain $-CO-CR_{13}=CR_{15}-NR_{20}-$, in which one of $R_{13}$ and $R_{15}$ represents $E_1$, then $E_1$ represents hydrogen, and (ii) represents a chain $-CR_{11}=CR_{13}-CR_{15}=N-$, then at least one of $R_{11}$, $R_{13}$ or $R_{15}$, which may be the same or different, represents $NR_{21}COR_{22}$, CN or $C_nH_xF_{(2n+1-x)}$, and pharmaceutically acceptable derivatives thereof.

According to the invention there is also provided a process for the production of a benzopyran of formula I, or a pharmaceutically acceptable derivative thereof, which comprises (a) cyclising a compound of formula II, or a suitable derivative thereof,

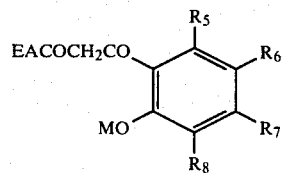

in which M represents a hydrogen atom or an alkali metal, and E, A, $R_5$, $R_6$, $R_7$ and $R_8$ are as defined above, (b) producing a compound of formula I, in which at least one of E and $E_1$ represents $-COOH$, by hydrolysing a compound of formula I in which the corresponding E, or $E_1$ represents a group hydrolysable to a $-COOH$ group, (c) producing a compound of formula I, in which at least one of E and $E_1$ represents 5-tetrazolyl, by reacting a compound of formula I, in which the corresponding E or $E_1$ represents $-CN$, with an azide in a solvent which is inert under the reaction conditions, (d) producing a compound of formula I, in which at least one of $R_{10}$, $R_{11}$, $R_{12}$, $R_{13}$, $R_{14}$, and $R_{15}$, represents $C_nH_xF_{(2n+1-x)}$, by reacting a compound of formula I, or a derivative thereof, in which the corresponding $R_{10}$, $R_{11}$, $R_{12}$, $R_{13}$, $R_{14}$, or $R_{15}$, represents $L_1$, wherein $L_1$ is a halogen atom, with a compound $C_nH_xF_{(2n+1-x)}L_2$, in which n and x are as defined above and $L_2$ represents chlorine, bromine or iodine, and if necessary or desired converting the compound of formula I to a pharmaceutically acceptable derivative thereof or vice versa.

The cyclisation of process (a) may be carried out by heating, or under basic or neutral conditions. It is however preferred to carry out the cyclisation in the presence of an acid, e.g. gaseous or aqueous HCl, and in a solvent which is inert under the reaction conditions, e.g. ethanol or dioxan. The reaction may be carried out at from about 20° to 150° C. When E in the compound of formula I represents $-COOH$, E in the compound of formula II preferably represents a carboxylic acid ester, e.g. an ethyl or methyl ester.

Groups hydrolysable to a $-COOH$ group in process (b) include carboxylic acid amides, nitriles, carboxylic halides and preferably carboxylic acid esters. The conditions of the hydrolysis depend on the nature of the group, but may be carried out using conventional techniques, for example under mildly basic conditions, e.g. using sodium carbonate, sodium hydroxide, sodium bicarbonate; or under acidic conditions, e.g. hydrogen bromide in acetic acid. For carboxylic acid esters, we prefer to carry out the hydrolysis under basic conditions, e.g. using sodium hydroxide in an alkanol, e.g. methanol. The hydrolysis may be carried out at a temperature of from about −5° to 120° C. depending on the compound and reagents used.

Suitable solvents which are inert under the reaction conditions of reaction (c) include those in which both reagents are soluble, e.g. N,N-dimethylformamide. Other solvents which may be mentioned include dimethylsulphoxide, tetrahydrofuran, diethylglycol and ethyl methyl glycol. The reaction is preferably carried out at a temperature of from about 20° to 130° C. for from about 1 to 20 hours. The azide used in the reaction is preferably ammonium or an alkali metal azide, e.g. sodium or lithium azide, but other azides, e.g. aluminium azide or the azides of nitrogen containing bases, e.g. mono-, di-, tri-, and tetra-methylammonium, anilinium, morpholinium and piperadinium azides, may also be used if desired. Where an azide other than that of an alkali metal is used, this azide may be prepared in the reaction mixture by double decomposition. The reaction may, if desired, be carried out in the presence of an electron acceptor, e.g. aluminium chloride, boron trifluoride, ethyl sulphonic acid or benzene sulphonic acid. As an alternative to the reaction conditions set out above the reaction may be carried out using hydrazoic acid (hydrogen azide) at a temperature of from about 20° to 150° C. in a suitable solvent, under greater than atmospheric pressure. When an azide other than hydrazoic acid is used, e.g. sodium azide, the product of the reaction will be the corresponding salt. This salt may be readily converted to the free acid by treatment with strong acid, e.g. hydrochloric acid.

Process (d) may be carried out in a solvent which is inert under the reaction conditions, e.g. hexamethylphosphoric triamide or dimethylformamide. The reaction may be carried out on elevated temperature of from about 50° to 200° C., and may, if desired, be carried out in an inert atmosphere and under pressure. The reaction is preferably carried out in the presence of a copper catalyst (Ullmann reaction). We prefer the groups $L_1$ and $L_2$, which may be the same or different, to be selected from bromine and iodine.

Compounds of formula II and derivatives thereof, may be prepared by reacting a carbanion derived from the corresponding compound of formula III, or a derivative thereof,

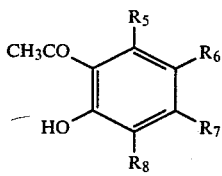

III in which $R_5$, $R_6$, $R_7$ and $R_8$ are as first defined above, with a compound of formula IV,

ECOL$_3$   IV in which $L_3$ represents a good leaving group and E is as defined above.

The reaction is preferably carried out in a solvent which is inert to the reaction conditions, e.g. an alkanol such as ethanol, or dimethylformamide. Carbanions of the compound of formula III may be formed by treating the compound of formula III with a strong, non-nucleophilic base, for example a metal alkoxide such as potassium t-butoxide or sodium ethoxide, or a metal hydride, for example sodium hydride. Preferably an excess, for example four equivalents of base for each equivalent of the compound of formula III is used. Good leaving groups that $L_3$ may represent include alkoxy, e.g. ethoxy. The reaction is preferably carried out at a temperature of from about 20° to 120° C. under an inert atmosphere and under anhydrous conditions.

The compounds of formula I in which at least one of E and $E_1$ represents a carboxylic ester may be made by processes analogous to those described under process (a) and, where appropriate, process (d).

The starting materials for process (c), i.e. compounds of formula I in which at least one of E and $E_1$ and $E_2$ represents —CN, may be prepared by reacting the compound of formula I in which the corresponding E or $E_1$ represents —CONH$_2$ with a dehydrating reagent. The reaction is preferably carried out using at least two molar equivalents of a dehydrating agent, e.g. POCl$_3$, per —CONH$_2$ group. The reaction may, if desired, be carried out in the presence of a proton acceptor, e.g. triethylamine. The reaction may be carried out in the presence of a solvent, e.g. N,N-dimethylformamide, dimethylsulphoxide, pyridine, benzene or hexamethyl phoshoric triamide, or an excess of the dehydrating agent may be used as the reaction medium. The reaction may be carried out at a temperature of from about 0° to 200° C. depending on the dehydrating agent used. When phosphorous oxychloride is used a temperature of from about 0° to 100° C. is preferred.

The compounds of formula I in which E or $E_1$ represents CONH$_2$ may be made in a conventional manner known per se from the corresponding carboxylic acid ester, e.g. by reaction of the ester with ammonia in an alkanol or dialkyl formamide solvent at a temperature of 0° to 120° C.

When L represents halide, the compounds of formula I in which E, or $E_1$ represents COL may be prepared by reacting the carboxylic acid with, for example, the appropriate thionyl halide or phosphoroyloxyhalide, under conventional conditions known per se. When L represents OCOCF$_3$, the mixed anhydride may be prepared from the corresponding carboxylic acid derivatives by conventional methods, e.g. by reaction with trifluoroacetic anhydride.

The compounds of formula III and IV are either known compounds or may be made from known compounds using for example techniques such as those described in the Examples.

The compounds of formula I and the intermediates therefor may be recovered from their reaction mixtures using conventional methods.

The process described above may produce the compound of formula I or a derivative thereof. It is also within the scope of this invention to treat any derivative so produced to liberate the free compound of formula I, or to convert one derivative into another.

Pharmaceutically acceptable derivatives of the compounds of formula I include pharmaceutically acceptable salts and, when any one of E or $E_1$ represents a carboxylic acid group, pharmaceuticaly acceptable esters or amides of the carboxylic acid groups.

Pharmaceutically acceptable salts of the compounds of formula I include ammonium, alkali metal (e.g. sodium, potassium and lithium) and alkaline earth metal (e.g. calcium or magnesium) salts, and salts with suitable organic bases, e.g. salts with hydroxylamine, lower alkylamines such as methylamine or ethylamine, with substituted lower alkylamines, e.g. hydroxy substituted alkylamines such as tris(hydroxymethyl)methylamine, or with simple monocyclic nitrogen heterocyclic compounds, e.g. piperidine or morpholine. Suitable esters include simple lower alkyl esters, e.g. the ethyl ester, esters derived from alcohols containing basic groups, e.g. di-lower alkyl amino substituted alkanols such as the beta-(diethylamino)ethyl ester, and acyloxy alkyl esters, e.g. a lower acyloxy-lower alkyl ester such as the pivaloyloxymethyl ester, or a bis-ester derived from a di-hydroxy compound, e.g. a di(hydroxy-lower alkyl)ester, e.g. the bis-2-oxapropan-1,3-diyl ester. The pharmaceutically acceptable acid addition salts of the basic esters, e.g. the hydrochloride, the hydrobromide, the oxalate, the maleate or the fumarate salts may also be used. The esters (when a —COOH group is present) may be made by conventionl techniques, e.g. esterification or transesterification. The amides (when a —COOH group is present) may be, for example, unsubstituted or mono- or di- C 1 to 6 alkyl amides and may be made by conventional techniques, e.g. reaction of an ester of the corresponding acid with ammonia or an appropriate amine.

The compounds of formula I and pharmaceutically acceptable salts, and, when E or $E_1$ is a —COOH group, pharmaceutically acceptable esters and amides thereof are useful because they possess pharmacological activity in animals; in particular they are useful because they inhibit the release and/or action of pharmacological mediators which result from the in vivo combination of certain types of antibody and specific antigen, e.g. the combination of reaginic antibody with specific antigen (see Example 27 of British Patent Specification No. 1,292,601). The new compounds have also been found to interfere with reflex pathways in experimental animals and man, and in particular those reflexes associated with lung function. In man, both subjective and objective changes which result from the inhalation of specific antigen by sensitised subjects are inhibited by prior administration of the new compounds. Thus the new compounds are indicated for use in the treatment of reversible airway obstruction and/or to prevent the secretion of excess mucus. The new compounds are thus indicated for the treatment of allergic asthma, so-called "intrinsic" asthma (in which no sensitivity to extrinsic antigen can be demonstrated), bronchitis, coughs and the nasal and bronchial obstructions associated with common colds. The new compounds may also be of value in the treatment of other conditions in which antigen-antibody reactions or excess mucus secretion are responsible for, or are an adjunct to, disease, for example, hay fever; certain eye conditions, e.g. trachoma; alimentary allergy, e.g. urticaria and atopic eczema; and gastrointestinal conditions, for example gastrointestinal allergy, especially in children, e.g. milk allergy, or ulcerative colitis.

For the above mentioned uses the doses administered will, of course, vary with the compound employed, the mode of administration and the treatment desired. However, in general, satisfactory results are obtained when the compounds are administered at the dosage of from 0.001 to 50 mg per kg of animal body weight in the test set out in Example 27 of British Patent Specification No 1,292,601. For man the indicated total daily dosage is in the range of from 0.01 mg to 1,000 mg, preferably from 0.01 mg to 200 mg and more preferably from 1 mg to 60 mg, which may be administered in divided doses from 1 to 6 times a day or in sustained release form. Thus unit dosage forms suitable for administration (by inhalation or oesophageally) comprise from 0.01 mg to 50 mg, preferably 0.01 mg to 20 mg, and more preferably from 0.01 mg to 10 mg, of the compound preferably admixed with a solid or liquid pharmaceutically acceptable diluent, carrier or adjuvant.

The compounds of formula I, and pharmaceutically acceptable salts, and, when E or $E_1$ is a —COOH group, pharmaceutically acceptable esters and amides thereof, have the advantage that they are more efficacious in certain pharmacological models, or are longer acting than compounds of similar structure to the compounds of formula I. Furthermore the compounds of formula I, and pharmaceutically acceptable salts, and, when E or $E_1$ is a —COOH group, pharmaceutically acceptable esters and amides thereof, are advantageous in that they are more efficacious in interfering with reflex pathways and in inhibiting the secretion of mucus than are compounds of similar structure to the compounds of formula I.

According to the invention there is also provided the use of compounds of formula I to make a pharmaceutical formulation for the treatment of asthma.

$R_5$, $R_6$, $R_7$, $R_8$, $R_{10}$, $R_{11}$, $R_{12}$, $R_{13}$, $R_{14}$, $R_{15}$, $R_{20}$, $R_{21}$, $R_{22}$ and $R_{23}$, when they represent alkyl preferably represent alkyl C1 to 8, more preferably alkyl C1 to 6, for example methyl, ethyl or propyl.

When one or more of $R_5$, $R_6$, $R_7$, $R_8$, $R_{20}$, $R_{21}$, $R_{22}$ or $R_{23}$, represents aryl, preferred groups include heteroaryl groups, e.g. pyridinyl, quinolinyl and isoquonolinyl, as well as homoaryl groups. Homoaryl groups include phenyl, naphthyl, anthracenyl and phenanthryl. The aryl groups may be substituted by one or more of alkoxy, e.g. ethoxy, methoxy; halogen, e.g. chlorine, bromine, iodine, nitro or nitrile. We particularly prefer compounds in which aryl represents phenyl.

The chain —X—$CR_{12}R_{13}$—$CR_{14}R_{15}$—$NR_{20}$— may be formed between any adjacent pair of $R_5$, $R_6$, $R_7$ and $R_8$. However, we prefer those compounds in which the chain is formed between $R_6$ and $R_7$, particularly those compounds in which —X— is bonded to $R_6$ and —$NR_{20}$— is bonded to $R_7$.

Chains —X—$CR_{12}R_{13}$—$CR_{14}R_{15}$—$NR_{20}$— that may be specifically mentioned include:
 —C($C_nH_xF_{(2n+1-x)}$)=CH—C(COOH)=N—;
 —C($NR_{21}COR_{22}$)=CH—C(COOH)=N—;
 —C(=$NOR_{23}$)—CH=C(COOH)—$NR_{20}$—;
 —CO—CH=CH—$NR_{20}$—;
 —C(CN)=CH—C(COOH)=N—; and
 —$CR_{13}$=$CR_{15}$—$NR_{20}$—,
in which one of $R_{13}$ and $R_{15}$ represents —COOH and the other represents hydrogen.

Halogens that $R_5$, $R_6$, $R_7$ or $R_8$ may represent include fluorine, bromine and iodine.

We prefer compounds of formula I in which $R_5$ represents hydrogen, hydroxy or alkoxy C1 to 6.

We prefer compounds of formula I in which $R_8$ represents alkyl C1 to 6, in particular propyl.

When one or more of $R_{10}$, $R_{11}$, $R_{12}$, $R_{13}$, $R_{14}$ or $R_{15}$, represents $C_nH_xF_{(2n+1-x)}$, n is preferably an integer from 1 to 6 inclusive, more preferably from 1 to 4 inclusive. We prefer compounds in which y is a larger integer than x. Particular groups that $C_nH_xF_{(2n+1-x)}$ may represent include those in which x is zero, for example 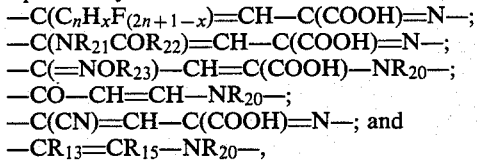 $CF_3$, $C_2F_5$ and $C_3F_7$. Other groups that may be mentioned include $CHF_2$ and $CH_2CF_3$.

When a geminal pair of $R_{10}$, $R_{11}$, $R_{12}$, $R_{13}$, $R_{14}$ and $R_{15}$, together with the carbon atom to which they are attached represents >C=O, we prefer either the pair $R_{10}$ and $R_{11}$ or the pair $R_{14}$ and $R_{15}$ together with the respective carbon atom to which they are attached to represent $>C=O$. We particularly prefer compounds of formula I in which X represents $C=O$.

We prefer compounds of formula I in which $NR_{21}COR_{22}$ represents $NHCOR_{22}$.

We prefer compounds of formula I in which X represents $>C=N-OR_{23}$.

When a vicinal pair of $R_{11}$, $R_{13}$, and $R_{15}$ form the chain $-CH=CH-CH=CH-$ which is substituted by $A_1E_1$, the corresponding vicinal pair of $R_{10}$, $R_{12}$, and $R_{14}$ preferably represents a single bond, such that the chain $-CH=CH-CH=CH-$ and the carbon atoms to which it is attached forms a six-membered carbocyclic aromatic ring. We prefer compounds in which the chain is connected between $R_{13}$ and $R_{15}$. We further prefer the chain $-CH=CH-CH=CH-$ to be substituted by a group $E_1$, preferably COOH.

When A or $A_1$ represents arylene, arylene groups that may be mentioned include hetero- as well as homoarylene groups. Heteroarylene groups include 2,3-, 2,4-, 2,5- and 2,6-pyridinyl; 2,3-, 2,4-, 2,5-, 2,6- and 2,7-quinolinyl and 1,3-, 1,4-, 1,5-, 1,6- and 1,7-isoquinoliny;. Homoarylene groups that A and $A_1$ may represent include 1,2-, 1,3- and 1,4-phenylene and 1,2-, 1,3-, 1,4-, 1,5-, 1,6- and 1,7-naphthalene. The arylene group may be substituted by one or more of alkoxy, e.g. ethoxy, methoxy; halogen, e.g. chlorine, bromine or iodine; nitro or nitrile. We particularly prefer compounds of formula I in which $A_1$ represents phenylene.

We prefer compounds in which A represents a single bond.

We prefer compounds of formula I in which m is an integer from 1 to 6 inclusive, preferably from 1 to 4 inclusive, e.g. 1, 2 or 3.

We prefer compounds of formula I in which E represents —COOH.

We prefer compounds of formula I which bear a single group $E_1$. We particularly prefer compounds in which one of $R_{13}$ or $R_{15}$ represents $E_1$, particularly —COOH.

As a group of preferred compounds, we provide the compounds of formula I in which an adjacent pair of $R_5$, $R_6$, $R_7$ and $R_8$ represents a chain $-CR_{10}R_{11}-CR_{12}R_{13}-CR_{14}R_{15}-NR_{20}-$, in which the chain is substituted by $-A_1E_1$, wherein either (a) $R_{10}$ and $R_{12}$ together form a single bond and $R_{14}$ and $R_{20}$ together form a single bond, or (b) $R_{12}$ and $R_{14}$ together form a single bond, the remainder of $R_{10}$, $R_{11}$, $R_{12}$, $R_{13}$, $R_{14}$ and $R_{15}$, which may be the same or different, independently represent hydrogen, alkyl, $NHCOR_{22}$, CN or $C_nH_xF_{(2n+1-x)}$; in addition a geminal pair of $R_{10}$, $R_{11}$, $R_{12}$, $R_{13}$, $R_{14}$ and $R_{15}$ together with the carbon atom to which they are attached may represent $C=O$ or $C=NOR_{23}$, A and $A_1$ each represent a single bond, when $R_{20}$ does not form a single bond with $R_{14}$, $R_{20}$ may represent hydrogen, alkyl, aryl or alkyl substituted by aryl, n, x, $R_{21}$, $R_{22}$ are as first defined above, the remainder of $R_5$, $R_6$, $R_7$ and $R_8$, which may be the same or different, each independently represent hydrogen, hydroxy, alkyl, alkoxy or alkyl substituted by alkoxy, E and $E_1$ represent —COOH, save that when the chain represents $-COCR_{13}=CR_{15}-NR_{20}-$, in which one of $R_{13}$ and $R_{15}$ represents $E_1$ and the other represents hydrogen or alkyl, then E represents hydrogen, and provided that when the chain represents $-CR_{11}=CR_{13}-CR_{15}=N-$, then at least one of $R_{11}$, $R_{13}$ or $R_{15}$, which may be the same or different represents $NHCOR_{22}$, CN or $C_nH_xF_{(2n+1-x)}$, and pharmaceutically acceptable derivatives thereof.

As a specific group of compounds, we provide compounds of formula I in which $R_6$ and $R_7$ together represent the chain $-C(C_nH_xF_{(2n+1-x)})=CR_{13}-CR_{15}=N-$, one of $R_{13}$ and $R_{15}$ is —COOH and the other is hydrogen, $R_5$ represents hydrogen $R_8$ represents alkyl C1 to 6, A represents a single bond, E represents —COOH, n and x are as first defined above, and pharmaceutically acceptable derivatives thereof.

As a group of preferred compounds we also provide the compounds of formula I in which an adjacent pair of $R_5$, $R_6$, $R_7$ and $R_8$ represents $CR_{13}=CR_{15}-NR_{20}-$, wherein one of $R_{13}$ and $R_{15}$ represents COOH and the other represents hydrogen, $R_{20}$ represents hydrogen or alkyl C1 to 6, A represents a single bond, E represents COOH, and pharmaceutically acceptable derivatives thereof.

According to our invention we also provide a pharmaceutical composition comprising (preferably less than 80%, and more preferably less than 50% by weight) of a compound of formula I, or a pharmaceutically acceptable salt, or where E is a —COOH group, ester or amide thereof, in combination with a pharmaceutically acceptable adjuvant, diluent or carrier. Examples of suitable adjuvants, diluents or carriers are:- for tablets, capsules and dragees; microcrystalline cellulose, calcium phosphate, diatomaceous earth, a sugar such as lactose, dextrose or mannitol, talc, stearic acid, starch, sodium bicarbonate and/or gelatin; for suppositories, natural or hardened oils or waxes; and for inhalation compositions, coarse lactose. The compound of formula I, or the pharmaceutically acceptable salt, or where E or $E_1$ is a —COOH group, ester or amide thereof, preferably is in a form having a mass median diameter of from 0.01 to 10 microns. The compositions may also contain suitable preserving, stabilising and wetting agents, solubilisers, sweetening and colouring agents and flavourings. The compositions may, if desired, be formulated in sustained release form. We prefer compositions which are designed to be inhaled.

The invention is illustrated, but in no way limited by the following Examples, in which temperatures are in degrees centigrade.

EXAMPLE 1

4-Oxo-10-propyl-6-(trifluoromethyl))-4H-pyrano[3,2-g]quinoline-2,8-dicarboxylic acid, disodium salt (a) 2-Ethyl 8-methyl 6-bromo-4-oxo-10-propyl-4H-pyrano[3,2-g]quinoline-2,8-dicarboxylate A solution of 2-ethyl 8-methyl 4,6-dioxo-10-propyl-4H-pyrano[3,2-g]quinoline-2,8-dicarboxylate (40 g, 0.108 m) and phosphorus oxybromide (62 g, 0.216M) in 1,2-dichloroethane (2.5 L) was heated and stirred at reflux for 3 hours. The mixture was cooled, filtered, and methanol (1 L) was added. The solution was evaporated to dryness and the residue was triturated with petroleum ether (40°-60°) to give the sub-title compound as orange needles, 21.8 g (45%) mp 177°-8°.

(b) 2-Ethyl 8-methyl-4-oxo-10-propyl-6(trifluoromethyl)-4H-pyrano[3,2,g]quinoline-2,8-dicarboxylate The product of step (a) (12.5 g, 28 mmol) was stirred with trifluoromethyl iodide (50 g, 25 mmol) and activated copper powder (50 g, prepared by precipitation from cupric sulphate with zinc) in hexamethylphosphoric triamide (200 ml) in a nitrogen atmosphere at 110° in a pressure vessel for 3 hours. The mixture was allowed to cool and was diluted with water (1 L) and the solid was separated. Dichloromethane was added to the solid and undissolved copper was filtered off. The organic filtrate was dried, filtered, and the filtrate was evaporated to dryness leaving a brown solid. This solid was chromatographed on silica eluting with ether/petroleum ether 60°-80° (3:1). Evaporation of the eluent gave a yellow solid 2.5 g (20%) mp 172°-3°.

(c) 4-Oxo-10-propyl-6-(trifluoromethyl)-4H-pyrano[3,2-g]quinoline-2,8-dicarboxylic acid A solution of the product of step (b) (2.4 g, 55 mmol) in boiling methanol (300 ml) was stirred at reflux while N/10 aqueous sodium hydroxide solution (110 ml) was added. After the addition the solution was heated at reflux for 30 minutes and was then poured into a large volume of acetone. The solid obtained was filtered off, dissolved in water, and the resulting solution was acidified with dilute HCl. The solid obtained was filtered off, washed well with water and was sucked dry. The product was crystallised from ethanol to give pale yellow needles, 1.6 g (73%) mp 248°-9°.

Analysis Found: C, 53.4; H, 2.9; N, 3.43% $C_{18}H_{12}F_3NO_6$ Requires: with 2.54% water C, 53.3; H, 2.95; N, 3.45%

(d) Disodium 4-oxo-10-propyl-6-(trifluoromethyl)-4H-pyrano[3,2-quinoline-2,8-dicarboxylate The product of step (c) (1.466 g, 3.711 mmol) was added to a solution of sodium hydrogen carbonate (0.6235 g, 7.422 mmol) in water (50 ml). The resulting solution was filtered through a glass filter and the filtrate was freeze-dried. The solid obtained was dried in vacuo to give the disodium salt of the title compound, 1.5 g (97%).

Analysis Found: C, 42.33; H, 2.09; N, 2.66% $C_8H_{10}F_3NNa_2O_6$ Requires: with 13.2% water C, 42.7; H, 1.97; N, 2.77%

EXAMPLE 2

6-(Heptafluoropropyl)-4-oxo-10-propyl-4H-pyrano[3,2-g] quinoline-2,8-dicarboxylic acid (a) 2-Ethyl 8-methyl 6-(heptafluoropropyl)-4-oxo-10-propyl-4H-pyrano[3,2-g]quinoline-2,8-dicarboxylate Activated copper powder (10 g) was washed several times with 0.02 molar ethylenediaminetetracetic acid solution and water, then filtered, washed with water and dried. The dry copper powder (10 g) the quinoline product of Example 12(a), (10 g), perfluoropropyl iodide (25 g) and hexamethylphosphoric triamide (100 ml) were placed in a 100 ml sealed tube and heated at 110° for 24 hours. The cooled mixture was poured into water (500 ml) and the mixture filtered. The residue was washed off the filter with methylene chloride leaving behind the copper. The methylene chloride was washed with water, dried and evaporated to leave a brown solid 11.1 g. Column chromatography using $SiO_2$ with $CH_2Cl_2$: toluene 9:1 as eluant produced a faster running product 2.5 g (21%). The product was recrystallised from acetone to leave the sub-title product as pale yellow plates 1.80 g mp 144°-145.5°.

(b) Disodium 6-(heptafluoropropyl)-4-oxo-10-propyl-4H-pyrano[3,2-g]quinoline-2,8-dicarboxylate The diester product of step (a) (1.79 g) was dissolved in methanol (50 ml) and heated under reflux. Sodium hydroxide solution (6.66 ml of 1M) wa added dropwise and heating continued for 30 minutes. The solvent was removed in vacuo and the product precipitated from methanol (50 ml) with ether (700 ml). A second precipitation from water (20 ml) with acetone (1000 ml) gave, after scratching and allowing to stand, a fine yellow powder. The powder was dissolved in water, filtered and then freeze dried to leave the disodium salt of the title compound, as an ochre powder, 1.30 g.

Analysis Found C 39.74; H 2.08; N 2.28; Req for 10.62% $H_2O$ C 39.77; H 1.65-2.82; N 2.32.

EXAMPLE 3

4-Oxo-6-(pentafluoroethyl)-10-propyl-4H-pyrano[3,2-g]quinoline-2,8-dicarboxylic acid (a) 2-Ethyl 8-methyl-4-oxo-6-(pentafluoroethyl)-10-propyl-4H-pyrano[3,2-g]quinoline-2,8-dicarboxylate MP 136°-139° was prepared using the method of Example 2(a), but substituting perfluoroethyl iodide for the perfluoropropyl iodide.

Analysis Theory C 54.21; H 3.72; N 2.8; Found 54.00; 3.79; 2.85.

(b) Disodium 4-oxo-6-(pentafluoroethyl)-10-propyl-4H-pyrano[3,2-g]quinoline-2,8-dicarboxylate was prepared by the method of Example 2(b) but using the product of step (a) of this Example as starting material.

Analysis Theory for 10.27$H_2O$ C 41.85; H 2.99; N 2.57; Found 41.64; 2.79; 2.52.

EXAMPLE 4

6-(Difluoromethyl)-4-oxo-10-propyl-4H-pyrano[3,2-g]quinoline-2,8-dicarboxylic acid (a) Diethyl 6-formyl-4-oxo-10-propyl-4H-pyrano[3,2-g]quinoline-2,8-dicarboxylate A mixture of diethyl 6-methyl-4-oxo-10-propyl-4H-pyrano[3,2-g]quinoline-2,8-dicarboxylate (19 g), selenium dioxide (20.99 g), and glacial acetic acid (950 ml) was heated on a steam bath with stirring for 2 hours. The resulting suspension was cooled, filtered and poured into brine (8 l). The resulting precipitate was filtered off and the crude product dissolved in $CH_2Cl_2$, filtered and evaporated to dryness to give 20.5 g of the crude product (20.5 g). This product was chromatographed using 25:1 $CH_2Cl_2$: ethyl acetate as the solvent, yielding 13.95 g of required product (71%).

(b) Diethyl 6-(difluoromethy)-4-oxo-10-propyl-4H-pyrano[3,2-g]quinoline-2,8-dicarboxylate To a solution of diethylaminosulphur trifluoride (0.6 ml) in dichloromethane (30 ml) at 25° was added dropwise a solution of the product of step (a) (2.0 g) in dichloromethane (20 ml). The mixture was stirred at 25° for 3 hours. A further quantity of diethylaminosulphur trifluoride (0.06 ml) was added and the mixture stirred at room temperature for a further 2 hours. The resulting mixture was poured into water and extracted with ethyl acetate. The ethyl acetate extracts were washed with brine, dried and evaporated to leave an orange solid 1.9 g. Chromatography on $SiO_2$, ethyl acetate/petroleum ether 1:2, followed by dry column $SiO_2$ toluene/ethyl acetate 1:9) produced 65% of the sub-title compound, 1.37 g.

NMR, UV and IR spectra were consistent with the required structure.

(c) Disodium 6-(difluoromethyl)-4-oxo-10-propyl-4H-pyrano[3,2-g]-quinoline-2,8-dicarboxylate.

To a stirred solution of the product of step (b) (1.31 g) in methanol (200 ml) under reflux was added sodium hydroxide solution (12.09 ml of 0.5M) dropwise. Heating was continued for 30 mins then the solvent evaporated. The residue was dissolved in water (6 ml) and this solution added dropwise to acetone (800 ml) with stirring. The precipitate was collected, washed with acetone and then dissolved in sterile water. The solution was filtered and then freeze-dried to leave the disodium salt of the title compound as an ochre powder 1.138 g Analysis Found C:45.42; H:2.78; N:2.71. Req. for 11.02% $H_2O$ C:45.66; H:2.34–3.55; N:2.95.

EXAMPLE 5

6,9-Di hydro-4,6-dioxo-10-propyl-4H,6H-pyrano[3,2-g]quinoline-2-carboxylic acid

(a) Ethyl, 4,6-dioxo-10-propyl-4H,6H-pyrano[3,2-g]quinoline-2-carboxylate

6-Acetyl-4-chloro-7-hydroxy-8-propylquinoline (9.64 g) and diethyl oxalate (43.4 ml) in dry dimethylformamide (150 ml) were added to ether washed 50% sodium hydride (7.71 g) in dry dimethylformamide (150 ml) under nitrogen with stirring. After stirring at room temperature for 5 hrs the whole was poured into ethyl acetate and treated with aqueous acetic acid. The organic layer was separated, washed well with water and dried. The solvent was evaporated to leave a diketone which was dissolved in glacial acetic acid (100 ml) containing a few drops of concentrated sulphuric acid and heated under reflux for 24 hours. The reaction mixture was poured into water and extracted with ethyl acetate. Some insoluble material was filtered off to give 1.3 g of product.

The ethyl acetate was washed well with water, dried and the solvent evaporated to leave 1.2 g of product. Both products were shown by thin layer chromatography to be identical and were combined. Total yield, 2.5 g.

A recrystallisation from ethanol gave the sub-title compound, mp 296° dec.

Analysis: Found: C: 65.8,%; H: 5,4%; N: 4.03%; $C_{18}H_{17}NO_5$ Required: C: 66.1%; H: 5.2%; N: 4.3%.

(b) 6,9-Dihydro-4,6-dioxo-10-propyl-b 4H,6H-pyrano[3,2-g]-quinoline-2 -carboxylic acid The product of step (a) (1.92 g) in methanol (100 ml) was treated dropwise with 0.1 M sodium hydroxide solution (58.7 ml) with stirring under reflux. The reaction mixture was heated under reflux with stirring for a further 0.5 hour after addition, cooled, filtered and the filtrate acidified with aqueous glacial acetic acid. The precipitated product was collected by filtration, washed well with water and dried to give 1.37 g of green solid. This was suspended in water (100 ml), treated with sodium bicarbonate (0.385 g) and filtered to remove some green tar. The filtrate was acidified with glacial acetic acid and the precipitated product collected by filtration, washed well with water and dried to give 1.16 g of the title product, mp 324°–327° dec.

Analysis:
Found: C: 63.88%; H: 4.67; N: 4.38; $C_{16}H_{13}NO_5$ Required: C: 64.2%; H: 4.35%; N: 4.68%.

(c) Sodium 6,9-dihydro-4,6-dioxo-10-propyl-4H,6H-pyrano[3,2-g]-quinoline-2-carboxylate The product of step (b) (0.833 g) and sodium bicarbonate (0.234 g) were stirred in water (100 ml) until complete solution was obtained. The whole was filtered and the filtrate freeze dried to give 0.851 g of the sodium salt of the title compound.

Analysis: Found: C: 53.53%; H: 4.51%; N: 3.9%; $C_{16}H_{12}NHaO_5.2H_2O$ Required: C: 53.78%; H: 4.48%: 3.92.%

EXAMPLE 6

6,9-Dihydro-4,6-dioxo-9-ethyl-10-propyl-4H,6Hpyrano-pyrano[3,2-g]-quinoline-2-carboxylic acid

(a) 6,9-Dihydro-4,6-dioxo-9-ethyl-10-propyl-4H,6H-pyrano[3,2-g]-quinoline-2-carboxylic acid Diethyl 6,9-dihydro-4,6-dioxo-9-ethyl-10-propyl-4H,6H-pyrano-[3,2 g]quinoline-2,8-dicarboxylate (13.5 g) and sodium bicarbonate (10.6 g) in ethanol (500 ml) and water (100 ml) were refluxed for 5 hours. The reaction mixture was poured into water (2 1), acidified, and the product which was the crude diacid obtained by filtration and drying in vacuo. The crude diacid was recrystallised from boiling dimethylformamide to give 4.9 g of the sub-title monoacid, mp 302° dec.

Analysis: Found: C: 65.5%; H: 5.5%; N: 4.5%. $C_{18}H_{17}NO_5$ Required: C: 66.0% H: 5.2% N: 4.3%

(b) Sodium 6,9-dihydro-4,6-dioxo-9-ethyl-10-propyl-4H,6H-pyrano-[3,2-gluguinoline-2-carboxylate The product of step (a) (4.736 g) and sodium bicarbonate (1.22 g) in water (150 ml) were stirred together until complete solution was obtained. The solution was filtered and the filtrate freeze dried to give 5.05 g of the sodium salt of the title compound.

Analysis: Found: C: 56.0%; H: 5.2%; N; 3.4%; $C_{18}H_{16}NNaO_5.2H_2O$ Requires: C: 56.1%; H: 5.2%; N: 3.6%.

EXAMPLE 7
6,9-dihydro-4,6-dioxo-9-phenylmethyl-10-propyl-4H-pyrano[3,2-g]quinoline-2-carboxylic acid (a) N-[2,4-diacetyl-5-hydroxyphenyl]formamide A mixture of formic acid (98%, 50 ml) and 1-[5-acetyl2-amino-4-hydroxyphenyl]ethanone (5.0 g) was heated at reflux for 2 hours. The solution was allowed to cool and the crystalline material was filtered off and dried in vacuo at 80° to give the required amide, 5.2 g (90%) mp 193°–4°.

Found: C 59.66; H 4.99; N 6.2%; $C_{11}H_{11}NO_4$ requires: C 59.7; H 4.97; N 6.3%.

(b) 6-Acetyl-7-hydroxy-1-phenylmethyl-4(1H)-quinolinone

A suspension of pre-washed sodium hydride (0.87 g, 0.036 mmol) was stirred at 0° in dry dimethylformamide under nitrogen while N-[2,4-diacetyl-5-hydroxyphenyl]formamide (4.0 g, 18 mmol) was added in small portions. After the addition was complete the mixture was allowed to stir at 0° for 30 minutes, then benzyl bromide (3.1g, 18 mmol) was added all at once. The mixture was stirred for 6 hours during which time the temperature was allowed to rise to 10°. The dark brown solution was poured into a large excess of water, the mixture was acidified to approximately pH 4.0, and was stirred overnight. The off-white solid was filtered off, washed well with water and was dried. The solid was crystallised as white needles 4.8 g (90%) mp 246°–7°.

Found: C 73.78; H 5.08; N 5.09%; $C_{18}H_{15}NO_3$ requires: C 73.7; H 5.1; N 4.78%.

(c) 6-Acetyl-1-phenylmethyl-7-(prop-2-enyloxy)-4(1H)-quinolinone

A mixture of 6-acetyl-7-hydroxy-1-phenylmethyl-4(1H)-quinolinone (6.3 g, 21.5 mmol), anhydrous potassium carbonate (2.97 g, 21.5 mmol) and 3-bromopropene (2.86 g, 2.36 mmol) was stirred at room temperature in dry dimethylformamide (100 ml) for 18 hours. The mixture was poured into a large excess of water and was stirred rapidly for 1 hour. The solid produced was filtered off and washed well with water. The yellow solid was dried to give the required quino- lone as a yellow powder 6.2 g (87%) mp 139°–140°.

Mass and n.m.r. spectra confirmed the structure.

(d) 6-Acetyl-7-hydroxy-1-phenylmethyl-8-(prop-2-enyl)-4(1H)-quinolinone

A solution of 6-acetyl-1-phenylmethyl-7-(prop-2-enyloxy)-4(1H)-quinolinone (6.0 g, 18 mmol) in N,N-diethylbenzeneamine (40 ml) was heated at reflux for 2 hours under nitrogen. The solution was cooled and was poured into a large volume of rapidly stirred petroleum ether (40°–60°). A buff solid was produced which was filtered off and dried in vacuo to give the required quinolinone, 5.5 g (91%) mp 123°–4°.

(e) 6-Acetyl-7-hydroxy-1-phenylmethyl-8-propyl-4(1H)-quinolinone

A solution of 6-acetyl-7-hydroxy-1-phenylmethyl-8-(prop-2-enyl)-4(1H)-quinolinone (5.0 g, 15 mmol) in ethanol (250 ml) was hydrogenated at room temperature and atmospheric pressure over 5% Palladium on charcoal catalyst (0.5 g) until hydrogen uptake was complete (45 minutes). The catalyst was removed by filtration and the filtrate was evaporated to dryness leaving the required quinolinone as a green oil, 4.2 g (84%).

(f) Ethyl 6,9-dihydro-4,6-dioxo-9-phenylmethyl-10-propyl-4H-pyrano[3,2-g]quinoline-2-carboxylate A solution of 6-acetyl-7-hydroxy-1-phenylmethyl-8-propyl-4(1H)-quinolinone (3.0 g, 8.9 mmol) in ethanol (100 ml) was added to a solution of sodium ethoxide (from sodium, 1.15 g) in ethanol (150 ml). The mixture was stirred for 10 minutes then diethyl oxalate (3.6 g, 24.6 mmol) was added all at once and the mixture was heated at reflux for 30 minutes. The solution was poured into a large excess of water and the resulting solution was acidified to pH 4.0 with dilute HCl. The mixture was extracted with chloroform and the extracts were washed with water, dried over $MgSO_4$, filtered and the filtrate was evaporated to dryness. The residue was dissolved in ethanol (40 ml) containing ethanolic HCl (1 ml) and the solution was heated at reflux for 30 minutes. The solution was cooled and the solid obtained was filtered off and was crystallised from ethanol to give the required pyranoquinoline as pale yellow prisms, 1.9 g (50%) m.p. 207°–8°.

Found: C 69.1; H 5.55; N 3.21%; $C_{25}H_{23}NO_5$ requires C 68.9; H 5.7; N 3.21%. with 1 mole $H_2O$

(g) 6,9-Dihydro-4,6-dioxo-9-phenylmethyl-10-propyl-4H-pyrano[3,2-g]quinoline-2-carboxylic acid A suspension of ethyl 6,9-dihydro-9-phenylmethyl-10-propyl-4H-pyrano[3,2-g]quinoline-2-carboxylate (1.8 g, 4.6 mmol) in 0.1 N aqueous sodium hydroxide solution (46.9 ml) containing ethanol (10 ml) was heated at reflux for 6 hours. The mixture was cooled, filtered and the filtrate was acidified and filtered. The solid obtained was dried (in vacuo) at 80° to give the required acid as a yellow powder 0.6 g (32%) mp >250°.

Mass and n.m.r. spectra confirmed the structure.

(h) Sodium 6,9-dihydro-4,6-dioxo-9-phenylmethyl-10-propyl-4H-pyrano[3,2-g]quinoline-2-carboxylate 6,9-Dihydro-4,6-dioxo-9-phenylmethyl-10-propyl-4H-pyrano[3,2-g]quinoline-2-carboxylic acid (0.4237 g, 1.09mmol) was dissolved in a solution of sodium bicarbonate (0.0915 g, 0.00109 M) in water (50 ml). The resulting solution was filtered and freeze-dried. The solid obtained was dried in vacuo at 80° to give the required sodium salt as a yellow powder, 0.43 g (96%) m.p. >250°.

Found: C 59.6; H 4.03; N 3.14%; $C_{28}H_{18}NNaO_5$ requires with 10.75% water
C 59.9; N 3.04%.

EXAMPLE 8
9-Ethyl-7,9-dihydro-6-methoxyimino-4-oxo-10-propyl-4H6H-pyrano-3,2-quinoline-2,8-dicarboxylic acid

(a) Diethyl-9-ethyl-b 7,9-dihydro-6-methoxyimino-4-oxo-10-propyl-4H,6H-pyrano[3,2-g]-quinoline-2,8-dicarboxylic acid Methoxamine hydrochloride (3.9 g) in ethanol (100 ml) was added dropwise with stirring to a refluxing suspension of diethyl 9-ethyl-7,9-dihydro-6-methoxyimino-4-oxo-10-propyl-4H,6H-pyrano[3,2-g]quinoline- 2,8-dicarboxylate (20 g) in ethanol (600 ml). After one hour, the suspension was cooled, evaporated and the resulting solid purified by preparative high performance liquid chromatography (HPLC), first using 30% ethyl acetate:70% petrol (bp 60°-80°) eluant, then dichloromethane:ethyl acetate 25:1, to give the sub-title product (2.5 g) mp 205°-7°.

(b) Disodium-9-ethyl-7,9-dihydro-6-methoxyimino-4-oxo-10-propyl-4H,6H-pyrano[3,2-g]quinoline 8-dicarboxylate Sodium hydroxide solution (0.1%, 105 ml) was added dropwise over 1.25 hour to a refluxing solution of the diester of step (a) (2.45 g) in methanol (350 ml). The solution was then cooled, evaporated, the resulting solid dissolved in water and freeze dried to give the disodium salt of the title compound (1.79 g). $C_{20}H_{18}N_2Na_2O_7.4.5H_2O$ Requires: C: 45.72 H:5.17 N:5.33 ; Found: C: 45.56 H:4.57 N:5.35%.

EXAMPLE 9

6-(N Methyl-N-acetylamino)-4-oxo-10-propyl-4H-pyrano[3,2-g]quinoline-2,8-dicarboxylic acid (a) Diethyl 6-(N-methyl-N-acetylamino)-4-oxo-10-propyl-4H-pyrano[3,2-g]quinoline-2,8-dicarboxylate A solution of diethyl 6-(N-methylamino)-4-oxo-10-propyl-4H-pyrano[3,2-g]quinoline-2,8-dicarboxylate (1.25 g) in acetic acid (25 ml) and acetic anhydride (25 ml) was refluxed for 12 hours, then the solution was poured into water, extracted with ethyl acetate and the extract washed with sodium bicarbonate solution, dried and evaporated to give an oil. The oil crystallised from ethanol to give the required amide, 0.56 g (41%) mp 164°-5° C.

Found: C 63.77; H 6.00; N 6.42%; $C_{24}H_{26}N_2O_7$ requires: C 63.42; H 5.75; N 6.17%.

(b) Disodium 6-(N-methyl-N-acetylamino-4-oxo-10-propyl-4H-pyrano[3,2-g]quinoline-2,8-dicarboxyl ate 0.10 M Sodium hydroxide solution (21.85 ml) was slowly added to a stirred refluxing solution of diethyl 6-(N-methyl-N-acetylamino)-4-oxo-10-propyl-4H-pyrano[3,2-g]quinoline-2,8-dicarboxylate (0.497 g), in ethanol (50 ml). After 2.5 hours the solvent was evaporated and water was added (30 ml). The disodium salt was precipitated by the addition of acetone (1 l.) filtered off and redissolved in a little water. The solution was freeze dried to give the disodium salt of the title compound as a light green fluffy solid 0.39 g (73%).

|        | C     | H    | N     |
|--------|-------|------|-------|
| Found: | 47.88 | 3.59 | 5.52% |

$C_{20}H_{16}N_2Na_2O_7$. 11.8% water requires: 47.88 4.50 5.58%;

EXAMPLE 10

6-Cyano-4-oxo-10-propyl-4H-pyrano[3,2-g]quinoline-2,8dicarboxylic acid (a) 2-(4-Acetyl-3-dihydroxy-2-propylphenylamino)4-oxo-1-pentanoic acid 4-Acetyl-3-hydroxy-2-propylaniline (38.9 g) and 4-oxo-1-pentanoic acid (21 g) were finely powdered together then heated on a steam bath until a melt was obtained. After 15 minutes further heating, the mass solidified. The mass was then cooled, triturated with ether and the powdered product was collected and dired to yield the sub-title compound 22.6 g, mp 145°-147°.

(b) Ethyl 6-acetyl-7-hydroxy-4-methyl-8-propylquinoline-2-carboxylate

Polyphosphoric acid (200 ml) was heated with stirring on a steam bath and the pentanoic acid derivative of step (a) (finely powdered, 22.0 g) added in portions to the hot acid. After about 45 minutes further heating and stirring the warm mixture was poured into water (3 l) and stirred vigorously for 10 minutes. Ethyl acetate extraction, drying of the organic fraction and evaporation gave a gum. The gum was suspended in ethanolic HCl and refluxed for 1 hour. Evaporation gave the sub-title compound, 8.0 g, mp 154°-155° from propan-2-ol.

(c) Diethyl 6-methyl-4-oxo-10-propyl-4H-pyrano[3,2-g]quinoline-2,8-dicarboxylate Sodium (2.925 g) was dissolved in dry ethanol (380 ml) and the product of step (b) (8 g) was added together with diethyl oxalate (8.7 ml). After 2 hours at reflux, the mixture was cooled and acidified with gaseous HCl, until the suspension was yellow and the pH about 2. The mixture was then refluxed 30 minutes, cooled and evaporated. The residue obtained was washed with dilute sodium bicarbonate solution, dried to give the sub-title compound, 7.8 g from ethanol, mp 183°-4°.

(d) Diethyl 6-cyano-4-oxo-10-propyl-4H-pyrano[3,2-g]quinoline-2,8-dicarboxylate

The diester from step (c) (3.97 g), selenium dioxide (4.0 ml) and g lacial acetic acid (200 ml) were heated on a steam bath for 2 hours with stirring, to give a solution. The cooled solution was evaporated to give a residue, extracted into chloroform, filtered and the filtrate evaporated to give 6.3 g of the aldehyde as an orange solid.

The crude aldehyde (6.3 g) was dissolved in formic acid (99%, 40 ml), treated with sodium formate (1.12 g) and hydroxylamine hydrochloride (11 ml) and stirred on a steam bath for 6 hours. A further portion of hydroxylamine hydrochloride (0.38 g) and sodium formate (0.56 g) was added and the reaction heated for a further 3 hours. The reaction mixture was cooled, poured into water and the sub-title compound isolated as a green-yellow solid, 1.15 g from ethanol, mp 207°-209°.

(e)
Disodium-6-cyano-4-oxo-10-propyl-4H-pyrano[3,2-g]quinoline-2,8-dicarboxylate Sodium hydroxide solution (0.2 M, 24.1 ml) was added dropwise to a suspension of the diester from step (d) (0.9837 g) suspended in refluxing methanol (50 ml), over a period of 3 hours. The mixture was refluxed for a further 2 hours, cooled and evaporated to a residue. The residue was dissolved in water (5 ml), precipitated with acetone, the precipitate redissolved in water (15 ml) and the resulting solution freeze dried to give the disodium salt of the title compound as a green powder, 0.4 g. Nmr (D$_2$O) δ, 0.9 (3H,t), 1.8 (2H, m), 3.5 (2H, t), 6.9(1H,s). 8.4 (2H,s).

EXAMPLE 11

4-Oxo-9-propyl-4H,6H-pyrano[2,3-f]indole-2,7-dicarboxylic acid (a) Ethyl 5-hydroxy-4-propyl-1H-indole-2-carboxylate Ethyl 5-hydroxy-4-(2-propenyl)-1H-indole-2-carboxylate (2.16 g) was dissolved in dry ethanol (100 ml) and hydrogenated at atmospheric pressure in the presence of 5% palladium on charcoal (0.2 g) until hydrogen uptake had ceased. The catalyst was filtered off, washed with hot ethanol, the filtrate evaporated and the residue recrystallised from aqueous ethanol to give 1.616 g of the desired product mp 185°-186°:
Elemental analysis: Found: C 68.07; H 6.96; N 5.48%; C$_{14}$H$_{17}$NO$_3$ Required: C 68.0 H6.88 ; N5.67%.

(b)
2-(2-Carboxy-4-propyl-1H-indole-5-yloxy)but-2-ene-1,4-dioic acid

The product of step a) (5.0 g) and dimethyl acetylenedicarboxylate (2.72 ml) were heated under reflux in ethanol (56 ml) with benzyl trimethylammonium hydroxide (2 drops) for 8 hours and left to stand at room temperature overnight. The reaction mixture was poured into water (100 ml), extracted with ethyl acetate (2×100 ml), washed with saturated brine solution (2×100 ml), and dried. The solvent was evaporated, and the residue was triturated with petroleum ether which was decanted off. The petroleum ether insoluble material was dissolved in ethanol (55 ml) and treated with sodium hydroxide (4.83 g) in water (55 ml). The resulting solution was heated under reflux for 2 hours, cooled, poured into water (100 ml), acidified, extracted with ethyl acetate (2×100 ml), washed with saturated brine (2×100 ml) and dried. The solvent was evaporated and the residue triturated with petroleum ether to give 6.3 g of the desired product as a mixture of E and Z acids.

(c) Diethyl 4-oxo-9-propyl-4H,6H-pyrano[2,3-f]indole-2,7-dicarboxylate

The mixture of E and Z acids from step b) (5.3 g) was treated with polyphosphoric acid (130 ml) and heated on the steam bath with stirring for 1 hour. The reaction mixture was cooled, poured onto ice-water (400 ml), stirred for 3 hours and the product collected by filtration, washed with water and dried to give the crude ring-closed diacid. This was treated with a saturated solution of hydrogen chloride gas in ethanol (150 ml) and heated under reflux for 2 hours. The solution was poured into water (300 ml) and the product which precipitated was collected by filtration and dried. Trituration with ethyl acetate gave 1.35 g of the required diester as an insoluble yellow powder. The ethyl acetate was evaporated and the residue eluted down a silica gel column using ether/petroleum ether (7.3) as eluant to give a further 0.5 g of the desired product. A sample was recrystallised from ethanol to give material mp 227°-228°.
Found: C 64.82; H 5.64; N 3.66%; C$_{20}$H$_{21}$NO$_6$ Required: C 64.7; H 5.66; N 3.77%.

(d)
Disodium-4-oxo-9-propyl-4H,6H-pyrano[2,3-f]indole-2,7-dicarboxylate

A solution of the diester from step c) (1.3 g) in glacial acetic acid (40 ml) and concentrated hydrochloric acid (13 ml) was heated under reflux for 16 hours. More concentrated hydrochloric acid (3 ml) was added and the solution heated under reflux for a further 8 hours. The reaction mixture was allowed to cool overnight and the insoluble product collected by filtration, washed with a little glacial acetic acid, then petroleum ether and dried at 100° in vacuo for 4 hours to give 1.008 g of the diacid, which contained a trace of monoester as shown by NMR and MS. The crude diacid was treated with sodium bicarbonate (0.537 g) in water (30 ml), the resulting solution filtered, and the filtrate treated with acetone until there was complete precipitation of the disodium salt. The salt was collected by filtration and dried to give 0.825 g of the desired product. The disodium salt (0.52 g) was dissolved in water (30 ml) and freeze dried to give 0.497 g of the disodium salt of the title compound.
Found: C 44.0; H 3.0; N 3.1; Na 11.2%; C$_{16}$H$_{11}$Na$_2$NO$_6$17%H$_2$O Required C 44.4 N 3.66 Na 10.61%

Thermogravimetric analysis showed 16.3% weight loss at 290°.

Thermogravimetric analysis at 200° showed 14.07% water.

EXAMPLE 12
6-Ethyl-4-oxo-9-propyl-4H-pyrano-[2,3-f]indole-2,7-dicarboxylic acid

(a)
6-Ethyl-4-oxo-9-propyl-4H-pyrano[2,3-f]indole-2,7-dicarboxylic acid

Diethyl 4-oxo-9-propyl-4H-pyrano[2,3-f]indole2,7-dicarboxylate (0.954 g) was added to ether washed 50% sodium hydride (0.136 g) suspended in dry dimethylformamide (60 ml) with stirring under nitrogen. The reaction mixture was stirred for 0.5 hours, ethyl bromide (0.21 ml) added and stirring continued for 24 hours. The reaction was poured into water and the product which had precipitated collected by filtration, washed with water and dried to give 0.45 g of diethyl 6-ethyl-4-oxo-9-propyl-4H-pyrano[2,3-f]indole-2,7-dicarboxylate as a pale yellow solid. The structure was confirmed by nmr and ms.

The aqueous filtrate was acidified and extracted with ethyl acetate which was washed with water and dried over magnesium sulphate. The solvent was evaporated to leave 0.3 g of 7-ethyl-6-ethyl-4-oxo-9-propyl-4H-pyrano [2,3-f]indole-2-7-dicarboxylic acid. The structure was confirmed by nmr and ms. The diethyl ester (0.57 g) and mono ester (0.34 g) were combined, dissolved in glacial acetic acid (30 ml) treated with concentrated hydrochloric acid (10 ml) and heated under reflux for 8 hours. More concentrated hydrochloric acid (8 ml) was added and refluxing continued overnight. The reaction mixture was allowed to cool to room temperature and the product which had precipitated collected by filtration, washed with a little glacial acetic acid, then petroleum ether and dried at 100° in vacuo to give 0.748 g of the sub-title compound as yellow needles.

(b) Disodium-6-ethyl-4-oxo-9-propyl-4H-pyrano[2,3-f]indole-2,7-dicarboxylate

The diacid product of step a) (0.738 g) was treated with sodium bicarbonate (0.362 g) in water (50 ml) and stirred until complete solution was obtained. The solution was filtered and the filtrate treated with acetone until complete precipitation of the disodium salt was achieved. This was collected by filtration, dissolved in water (50 ml) and freeze-dried to give 0.648 g of the sub-title product as a yellow powder.

Elemental analysis: Found: C 46.6; N 2.94; $C_{18}H_{15}Na_2NO_6$ 15.8%$H_2O$ Required: C 46.9;N 3.05%.

Gravimetric analysis at 200° showed 15.8% weight loss.

EXAMPLE 13

4-Oxo-9-propyl-4H,8H-pyrano[3,2-f]indole-2,7-dicarboxylic acid (a) Ethyl 6-(2-propenyloxy)-1H-indole-2-carboxylate Ethyl 6-hydroxy-1H-indole-2-carboxylate (4.6 g, 0.02 M) was heated under reflux with allylbromide (3 g, 2.2 ml, 0.025 M), $K_2CO_3$ (4.14 g 0.03 M) and acetone (150 ml) for 20 hours. On cooling the mixture was poured into brine and extracted into ethyl acetate, washed with brine, dried over magnesium sulphate and evaporated to dryness. The resulting crude brown solid was purified by extraction into hot 60°-80° petroleum ether to yield a yellow solid which was dried in vacuo, 4 g, 72%, mp 89°-91°.

(b) Ethyl 6-hydroxy-7-(2-propenyl)-1H-indole-2-carboxylate

The product of step a) (2.55 g, 10 mmol) was heated at 205°, under $N_2$, with stirring for 0.75 hour. The product obtained on cooling was powdered under petroleum ether (60°-80°) to give the sub-title compound as a pale brown solid which was recrystallised from aqueous ethanol, 2.14 g (84%), mp 146°-147°.

(c) Ethyl 6-hydroxy-7-propyl-1H-indole-2-carboxylate

The product of step b) was dissolved in dry ethanol (350 ml), treated with 10% Pd/C (0.3 g) and hydrogenated at 35 psi at room temperature until $H_2$ uptake ceased (1.5 hours). The catalyst was filtered off and the filtrate evaporated to dryness.

The light brown product was purified by extraction into hot 60°-80° petroleum ether to give the sub-title compound as a pale yellow powder 2.94 g, (84%) mp 125°-127°.

(d) Dimethyl 2-(2-ethoxycarbonyl-7-propyl-1H-indol-5-loxy-but-2-ene-1,4-dioate

The product of step (c) (0.6 g, 0.0024 M), dimethyl acetylene dicarboxylate (0.33 ml, 0.0027 M) and "Triton B" (2 drops) were heated under reflux for 6 hours in dry ethanol (10 ml). The reaction mixture was cooled, NaOH (0.6 g, 14.6 mmol) in water (6 ml) was added and refluxing continued for 1 hour. The whole was cooled, poured into dil. HCl, extracted into ethyl acetate and washed with brine before drying over $MgSO_4$ and evaporating to dryness to yield the sub-title compound as a pale yellow solid, 0.7 g, (86%).

(e) Diethyl 4-oxo-9-propyl-4H,8H-pyrano[3,2-f]indole-2-dicarboxylate

The product of step d) (1.7 g, 5 mmol) was stirred in polyphosphoric acid (15 g) on a steam bath for 1 hour. The reaction mixture was then poured onto ice and extracted with ethyl acetate, washed with brine, dried over MgSO4 and evaporated to dryness. The brown solid obtained (the free di-acid corresponding to the title compound) was treated with ethanolic HCl (30 ml) and heated under reflux conditions for 1.5 hours. A pale yellow precipitate formed on cooling and was filtered off ( 90 mgs). The filtrate was poured into water, extracted into ethyl acetate, washed, dried and evaporated to dryness. The resulting crude brown solid was eluted down a silica gel column using ether as elutant to give a yellow solid 130 mgs. Total yield of sub-title compound 220 mg 12%. mp 229°-231°.

(f) Disodium 4-oxo-9-propyl-4H,8H-pyrano[3,2-f]indole-2,7-dicarboxylate

The product of step e) (0.435 g; 12 mmol) was heated under reflux in methanol (20 ml). N/10 NaOH (23.5 ml 2.4 mmol) was added dropwise to the solution over a 35 minute period and the reaction mixture was heated for a further 25 minutes. After cooling to room temperature, the methanol was removed by evaporation and the aqueous solution was poured into acetone. The bright yellow precipitate was filtered off and dried in vacuo. 0.39 g (95%). mp>300° C.

We claim:
1. A benzopyran of formula I,

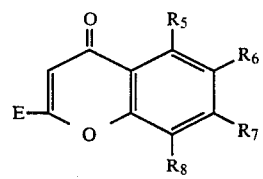

wherein $R_6$ and $R_7$ represent the chain —X—$CR_{12}R_{13}$—$CR_{14}R_{15}$—$NR_{20}$— in which the chain is substituted by $E_1$, X represents $CR_{10}R_{11}$ or a single bond, and either (a) $R_{14}$ and $R_{20}$ together form a single bond and $R_{10}$ and $R_{12}$ together form a single bond, or (b) $R_{12}$ and $R_{14}$ together form a single bond, the remainder of $R_{10}$, $R_{11}$, $R_{12}$, $R_{13}$, $R_{14}$ and $R_{15}$, which may be the same or different, independently represent hydrogen, alkyl $C_1$ to $C_6$, $NR_{21}COR_{22}$, CN or $C_nH_xF_{(2n+1-x)}$; in addition $R_{10}$ and $R_{11}$, together with the carbon atom to which they are attached, may represent C=O or C=N-$OR_{23}$;

n represents an integer from 1 to 10 inclusive, x represents 0 or an integer from 1 to 2n inclusive, when $R_{20}$ does not form a single bond with $R_{14}$, $R_{20}$ may represent hydrogen, alkyl $C_1$ to $C_6$, phenyl or alkyl $C_1$ to $C_6$ substituted by phenyl, $R_{21}$, $R_{22}$ and $R_{23}$, which may be the same or different, independently represent hydrogen, alkyl $C_1$ to $C_6$ or phenyl;

R$_5$ and R$_8$, which may be the same or different, each independently represent hydrogen, hydroxy, alkoxy C$_1$ to C$_6$, alkyl C$_1$ to C$_6$, phenyl, or alkyl C$_1$ to C$_6$ substituted by phenyl, E and E$_1$ represent —COOH, provided that when the chain —X—CR$_{12}$R$_{13}$—CR$_{14}$R$_{15}$—NR$_{20}$—

(i) represents a chain —CO—CR$_{13}$=CR$_{15}$—NR$_{20}$—, in which one of R$_{13}$ and R$_{15}$ represents E$_1$, then E$_1$ represents hydrogen, and (ii) represents a chain —CR$_{11}$=CR$_{13}$—CR$_{14}$=N—, then at least one of R$_{11}$, R$_{13}$ or R$_{15}$, which may be the same or different, represents NR$_{21}$COR$_{22}$, CN or C$_n$H$_x$F$_{(2n+1-x)}$, and pharmaceutically acceptable derivatives thereof.

2. A benzopyran according to claim 11, wherein

R$_6$ and R$_7$ together represent the chain —C(C$_n$H$_x$F$_{(2n+1-x)}$)=CR$_{13}$—CR$_{15}$=N—, in which the N atom is bonded to R$_7$, one of R$_{13}$ and R$_{15}$ is —COOH and the other is hydrogen, R$_5$ represents hydrogen, R$_8$ represents alkyl C$_1$ to C$_6$, n and x are as defined in claim 1, and pharmaceutically acceptable derivatives thereof.

3. A benzopyran according to claim 1, wherein X represents CR$_{10}$R$_{11}$.

4. A benzopyran according to claim 1, wherein —X— is bonded to R$_6$ and —NR$_{20}$— is bonded to R$_7$, and pharmaceutically acceptable derivatives thereof.

5. A benzopyran according to claim 1, wherein the compound of formula I is

4-Oxo-10-propyl-6-(trifluoromethyl))-4H-pyrano[3,2-g]quinoline-2,8-dicarboxylic acid and pharmaceutically acceptable derivatives thereof 6. A benzopyran according to claim 1, which is:

6-(Heptafluoropropyl)-4-oxo-10-propyl-4H-pyrano[3,2-g]quinoline-2,8-dicarboxylic acid, 4-Oxo-6-(pentafluoroethyl)-10-propyl-4H-pyrano[3,2-g]quinoline-2,8-dicarboxylic acid, 6-(Difluoromethyl)-4-oxo-10-propyl-4H-pyrano[3,2-g]quinoline-2,8-dicarboxylic acid, 6,9-Dihydro-4,6-dioxo-10-propyl-4H,6H-pyrano[3,2-g]quinoline-2-carboxylic acid, 6,9-Dihydro-4,6-dioxo-9-ethyl-10-propyl-4H,6H-pyrano[3,2-g]-quinoline-2-carboxylic acid, 9-Ethyl-7,9-dihydro-6-methoxyimino-4-oxo-10-propyl-4H,6H-pyrano[3,2-g]quinoline-2,8-dicarboxylic acid, 6-(N-Methyl-N-acetylamino)-4-oxo-10-propyl-4H-pyrano[3,2-g]quinoline-2,8-dicarboxylic acid, 6-Cyano-4-oxo-10-propyl-4H-pyrano[3,2-g]quinoline-2,8dicarboxylic acid, 4-Oxo-9-propyl-4H,6H-pyrano[2,3-f]indole-2,7dicarboxylic acid, 6-Ethyl-4-oxo-9-propyl-4H-pyrano[2,3-f]indole-2,7dicarboxylic acid, 4-Oxo-9-propyl-4H,8H-pyrano[3,2-f]indole-2,7dicarboxylic acid or and pharmaceutically acceptable derivatives thereof 7. An anti-asthmatic pharmaceutical composition which comprises an anti-asthmatic effective amount of at least one compound according to claim 1 in association with a pharmaceutically acceptable adjuvant, diluent, or carrier.

8. A method of treating asthma which comprises administering an anti-asthmatic effective amount of a compound according to claim 1 to a patient suffering from such a condition.

* * * * *